United States Patent
Goetz et al.

(10) Patent No.: US 9,681,968 B2
(45) Date of Patent: Jun. 20, 2017

(54) STENT WHICH IS REDUCEABLE AGAIN IN ITS DIAMETER FROM AN EXPANDED STATE IN A CONTROLLED MANNER

(75) Inventors: Wolfgang Goetz, Regensburg (DE); Hou Sen Lim, Singapore (SG)

(73) Assignee: VENUS MEDTECH (HANGZHOU), INC., Hangzhou (CN)

( * ) Notice: Subject to any disclaimer, the term of this patent is extended or adjusted under 35 U.S.C. 154(b) by 215 days.

(21) Appl. No.: 12/920,501

(22) PCT Filed: Mar. 2, 2009

(86) PCT No.: PCT/EP2009/001464
§ 371 (c)(1),
(2), (4) Date: Oct. 29, 2010

(87) PCT Pub. No.: WO2009/109348
PCT Pub. Date: Sep. 11, 2009

(65) Prior Publication Data
US 2011/0040366 A1    Feb. 17, 2011

(30) Foreign Application Priority Data

Mar. 2, 2008 (DE) .................. 10 2008 012 113
Mar. 10, 2008 (DE) .................. 10 2008 013 381
Mar. 12, 2008 (DE) .................. 10 2008 013 948

(51) Int. Cl.
*A61F 2/06* (2013.01)
*A61F 2/95* (2013.01)
(Continued)

(52) U.S. Cl.
CPC .............. *A61F 2/95* (2013.01); *A61F 2/2418* (2013.01); *A61F 2/2439* (2013.01); *A61F 2/91* (2013.01);
(Continued)

(58) Field of Classification Search
CPC .. A61F 2/95; A61F 2/2439; A61F 2/91; A61F 2002/9505; A61F 2/915;
(Continued)

(56) References Cited

U.S. PATENT DOCUMENTS 4,913,141 A * 4/1990 Hillstead .................. A61F 2/88
606/194
5,035,706 A * 7/1991 Giantureo ................. A61F 2/86
606/198
(Continued)

FOREIGN PATENT DOCUMENTS

CN    1961983 A      5/2007
DE    199 36 207 A1  2/2001
(Continued)

OTHER PUBLICATIONS

Machine translation of CN 1961983; Wen Ning; published May 16, 2007.*
PCT International Search Report, May 28, 2009.

*Primary Examiner* — Amy R Weisberg
(74) *Attorney, Agent, or Firm* — Hamre, Schumann, Mueller & Larson, P.C.

(57) ABSTRACT

A catheter for detachably receiving an expandable and/or decollapsible or unfoldable, respectively, implant, in particular a stent may include at least one assembly for controlling the expansion and/or the unfolding or decollapsing, respectively, of the implant from a first diameter to a second diameter and/or its return back from the second diameter to the first diameter. Furthermore, an implant, in particular a stent, and a set including a catheter and an implant are proposed.

21 Claims, 5 Drawing Sheets

(51) Int. Cl.
*A61F 2/24* (2006.01)
*A61F 2/91* (2013.01)
*A61F 2/915* (2013.01)
*A61M 25/06* (2006.01)
*A61F 2/88* (2006.01)

(52) U.S. Cl.
CPC .............. *A61F 2/915* (2013.01); *A61M 25/06* (2013.01); *A61F 2/88* (2013.01); *A61F 2002/9155* (2013.01); *A61F 2002/9505* (2013.01); *A61F 2002/9511* (2013.01); *A61F 2002/9528* (2013.01); *A61F 2002/9534* (2013.01); *A61F 2230/0054* (2013.01); *A61F 2230/0091* (2013.01)

(58) Field of Classification Search
CPC ............ A61F 2/2418; A61F 2230/0054; A61F 2230/0091; A61F 2002/9534; A61F 2002/9528; A61F 2/88; A61F 2002/9511; A61F 2002/9155; A61M 25/06
USPC ................ 606/108; 623/1.11–1.12, 1.23
See application file for complete search history.

(56) References Cited

U.S. PATENT DOCUMENTS

| | | | | |
|---|---|---|---|---|
| 5,290,305 | A * | 3/1994 | Inoue | A61F 2/07 600/37 |
| 5,411,552 | A | 5/1995 | Andersen et al. | |
| 5,647,857 | A | 7/1997 | Anderson et al. | |
| 5,776,186 | A * | 7/1998 | Uflacker | A61F 2/07 128/898 |
| 5,840,081 | A | 11/1998 | Andersen et al. | |
| 6,015,422 | A * | 1/2000 | Kerr | A61F 2/95 606/191 |
| 6,071,285 | A * | 6/2000 | Lashinski | A61F 2/958 604/103.04 |
| 6,168,614 | B1 | 1/2001 | Andersen et al. | |
| 6,302,891 | B1 * | 10/2001 | Nadal | A61F 2/962 606/108 |
| 6,352,553 | B1 | 3/2002 | van der Burg et al. | |
| 6,517,550 | B1 * | 2/2003 | Konya | A61B 17/32056 606/113 |
| 6,716,238 | B2 * | 4/2004 | Elliott | A61F 2/95 623/1.11 |
| 7,018,406 | B2 | 3/2006 | Seguin et al. | |
| 7,252,680 | B2 * | 8/2007 | Freitag | A61F 2/88 606/108 |
| 7,837,727 | B2 * | 11/2010 | Goetz | A61F 2/2418 623/1.15 |
| 7,947,075 | B2 * | 5/2011 | Goetz et al. | 623/2.18 |
| 8,109,986 | B2 * | 2/2012 | Styrc | A61F 2/0095 623/1.1 |
| 8,142,488 | B2 * | 3/2012 | Reynolds | A61F 2/91 623/1.11 |
| 2002/0029076 | A1 * | 3/2002 | Yee | A61F 2/95 623/1.11 |
| 2002/0038144 | A1 * | 3/2002 | Trout, III | A61F 2/07 623/1.15 |
| 2003/0050684 | A1 * | 3/2003 | Abrams | A61F 2/95 623/1.11 |
| 2003/0114913 | A1 | 6/2003 | Spenser et al. | |
| 2004/0116996 | A1 | 6/2004 | Freitag | |
| 2005/0070895 | A1 * | 3/2005 | Ryan | A61B 18/14 606/48 |
| 2005/0075731 | A1 | 4/2005 | Artof et al. | |
| 2005/0096650 | A1 * | 5/2005 | Ouchi | A61B 18/1402 606/47 |
| 2005/0119722 | A1 * | 6/2005 | Styrc | A61F 2/95 623/1.12 |
| 2005/0197695 | A1 | 9/2005 | Stacchino et al. | |
| 2006/0155366 | A1 | 7/2006 | LaDuca et al. | |
| 2006/0293743 | A1 * | 12/2006 | Andersen | A61F 2/07 623/1.13 |
| 2007/0043423 | A1 * | 2/2007 | Grewe | A61F 2/885 623/1.11 |
| 2007/0100427 | A1 * | 5/2007 | Perouse | A61F 2/07 623/1.11 |
| 2007/0233223 | A1 * | 10/2007 | Styrc | A61F 2/2439 623/1.11 |
| 2008/0140178 | A1 * | 6/2008 | Rasmussen | A61F 2/95 623/1.11 |
| 2008/0140189 | A1 | 6/2008 | Nguyen et al. | |
| 2008/0147180 | A1 | 6/2008 | Ghione et al. | |
| 2008/0147181 | A1 | 6/2008 | Ghione et al. | |
| 2008/0147182 | A1 | 6/2008 | Righini et al. | |
| 2008/0154351 | A1 * | 6/2008 | Leewood | A61F 2/86 623/1.2 |
| 2008/0208309 | A1 * | 8/2008 | Saeed | A61F 2/07 623/1.11 |
| 2008/0255662 | A1 | 10/2008 | Stacchino et al. | |
| 2008/0262507 | A1 | 10/2008 | Righini et al. | |
| 2008/0262603 | A1 | 10/2008 | Giaquinta et al. | |
| 2008/0275540 | A1 * | 11/2008 | Wen | A61F 2/2418 623/1.26 |
| 2009/0018570 | A1 | 1/2009 | Righini et al. | |
| 2009/0048656 | A1 * | 2/2009 | Wen | A61F 2/2418 623/1.12 |
| 2009/0069886 | A1 | 3/2009 | Suri et al. | |
| 2009/0069887 | A1 | 3/2009 | Righini et al. | |
| 2009/0069890 | A1 | 3/2009 | Suri et al. | |
| 2009/0099574 | A1 * | 4/2009 | Fleming, III | A61B 17/221 606/113 |
| 2009/0099640 | A1 * | 4/2009 | Weng | A61F 2/95 623/1.11 |
| 2009/0099653 | A1 | 4/2009 | Suri et al. | |
| 2009/0234428 | A1 * | 9/2009 | Snow | A61F 2/95 623/1.11 |
| 2009/0287296 | A1 | 11/2009 | Manasse | |
| 2010/0016944 | A1 * | 1/2010 | Styrc | A61F 2/95 623/1.12 |
| 2010/0094400 | A1 * | 4/2010 | Bolduc | A61B 17/00234 623/1.11 |
| 2010/0114290 | A1 * | 5/2010 | Rasmussen | A61F 2/07 623/1.11 |
| 2010/0114291 | A1 * | 5/2010 | Kolbel | A61F 2/07 623/1.12 |
| 2010/0161045 | A1 | 6/2010 | Righini | |
| 2010/0179636 | A1 * | 7/2010 | Mayberry | A61F 2/954 623/1.11 |
| 2010/0268315 | A1 * | 10/2010 | Glynn | A61F 2/95 623/1.11 |
| 2010/0268322 | A1 * | 10/2010 | Styrc | A61F 2/95 623/1.15 |
| 2010/0280589 | A1 * | 11/2010 | Styrc | A61F 2/2412 623/1.12 |
| 2011/0054585 | A1 * | 3/2011 | Osborne | A61F 2/95 623/1.11 |
| 2011/0160835 | A1 * | 6/2011 | Licata | A61F 2/95 623/1.11 |
| 2011/0208283 | A1 * | 8/2011 | Rust | A61F 2/2418 623/1.11 |
| 2011/0313503 | A1 * | 12/2011 | Berra | A61F 2/07 623/1.11 |
| 2011/0313505 | A1 * | 12/2011 | McHugo | A61F 2/954 623/1.12 |
| 2012/0010696 | A1 * | 1/2012 | Greenberg | A61F 2/07 623/1.12 |
| 2012/0029526 | A1 * | 2/2012 | Hewitt | A61B 17/00234 606/113 |
| 2012/0277848 | A1 * | 11/2012 | Roeder | A61F 2/07 623/1.13 |
| 2014/0296905 | A1 * | 10/2014 | Dela | A61F 2/01 606/200 |

(56) References Cited

U.S. PATENT DOCUMENTS

2014/0336611 A1* 11/2014 Lizak ............... A61B 17/32056
604/500

FOREIGN PATENT DOCUMENTS

| | | |
|---|---|---|
| DE | 101 18 944 A1 | 10/2002 |
| DE | 103 35 948 B3 | 2/2005 |
| EP | 0 732 087 A1 | 9/1996 |
| EP | 1 935 377 B1 | 6/2008 |
| EP | 1 935 378 A1 | 6/2008 |
| EP | 1 967 164 A2 | 9/2008 |
| EP | 1 985 259 A1 | 10/2008 |
| EP | 1 994 950 A2 | 11/2008 |
| EP | 2 033 581 A1 | 3/2009 |
| EP | 2 033 593 A1 | 3/2009 |
| EP | 2 033 597 A1 | 3/2009 |
| EP | 2 047 824 A1 | 4/2009 |
| EP | 2 119 417 A2 | 11/2009 |
| EP | 2 153 799 A1 | 2/2010 |
| EP | 2 201 911 A2 | 6/2010 |
| EP | 2 014 257 B1 | 9/2010 |
| EP | 2 229 921 A1 | 9/2010 |
| EP | 2 238 947 A2 | 10/2010 |
| FR | 2 688 688 A1 | 9/1993 |
| WO | 97/21402 A1 | 6/1997 |
| WO | 01/08599 A1 | 2/2001 |
| WO | 2006/076325 A1 | 7/2006 |

* cited by examiner

STENT WHICH IS REDUCEABLE AGAIN IN ITS DIAMETER FROM AN EXPANDED STATE IN A CONTROLLED MANNER

CROSS-REFERENCE TO RELATED APPLICATION

This application is filed under 35 U.S.C. §371 as a U.S. national phase application of PCT/EP2009/001464, having an international filing date of Mar. 2, 2009, which claims the benefit of German Patent Application Nos. 10 2008 012 113.4, having a filing date of Mar. 2, 2008; 10 2008 013 381.7, having a filing date of Mar. 10, 2008; and 10 2008 013 948.3, having a filing date of Mar. 12, 2008, all of which are incorporated herein by reference.

TECHNICAL FIELD

The present invention relates to a catheter, an implant, and a set including a catheter and an implant.

BACKGROUND

In medicine, stents, or implants in general, are used for keeping vessels (especially: blood vessels) or tubes (especially trachea, esophagus, stomach, intestine, urethra, ureter) open. They are inserted or advanced, respectively, to the implantation site in a folded or collapsed, respectively, or crimped manner by using a catheter. At this site, the unfolding or decollapsing, respectively, of folded or collapsed stents is effected by removing an outer sleeve, which is arranged over or about the folded or collapsed stent, by means of reset or restoring forces; or by means of a balloon arranged inside the stent, which expands the stent encircling or encompassing the balloon when being inflated or blown up, respectively. Usually, stents are made from bio-compatible steel. Once unfolded or decollapsed, respectively, or expanded, it is difficult or impossible to return the stent back to a reduced diameter. The latter is regularly important if a stent which is placed incorrectly in the target organ (vessel or another organ, see above) has been unfolded or expanded; a stent which has been expanded or unfolded at the wrong site can generally not be re-implanted without having the possibility to reduce its diameter.

It may be desirable to propose a catheter for returning an implant, in particular a stent, back to a reduced diameter after having unfolded and/or expanded the stent at the implantation site. In addition, an implant, in particular a stent, which is suited hereto shall be proposed. Furthermore, a set including a catheter and an implant shall be presented.

SUMMARY

Thus, according to the invention, there is proposed a catheter for detachably receiving an expandable and/or decollapsible or unfoldable, respectively, implant, in particular a stent, wherein the catheter comprises at least one means for controlling the expansion and/or the unfolding or decollapsing, respectively, of the implant from a first diameter to a second diameter and/or for returning back the implant from the second diameter to the first diameter; or is prepared for receiving such a means.

According to the invention, expanding or unfolding or decollapsing, respectively, is understood as enlarging the diameter of the implant. Thereby, the non-expanded or non-unfolded or non-decollapsed, respectively, diameter (which can also be referred to as a first diameter, wherein also another diameter which is smaller than the second diameter mentioned below can be understood as a first diameter in the sense of the present invention) can be a diameter of the implant immediately before its insertion into the patient's body. In returning the diameter back from a second diameter (which is larger than the first diameter) to an arbitrary reduced diameter (the first diameter), the diameter is diminished or reduced, respectively. Returning (back) can be accomplished by a (completely or partly) re-folding or a reversed expanding procedure. According to the invention, during the returning procedure, the implant does not necessarily have to be brought into a shape that it occupied or passed through during unfolding or expanding.

In case a diameter of the implant could not be determined, expanding or unfolding or decollapsing, respectively, is understood as an increase in a direction or dimension of the implant which effects an elongation of a periphery or circumference, respectively, of the implant in a plane perpendicular to the longitudinal direction of the implant explained further below.

According to the invention, receiving an implant by the catheter is understood as any functional connection between the implant and the catheter. Thereby, a transmission of power or forces, respectively, can take place, but does not have to take place. The connection can be provided as a frictional or form closure connection or neither as a frictional nor as a form closure connection.

According to the invention, "controlling" also includes adjusting or setting or regulating, respectively. Thereby, it can be adjusted or set or regulated, respectively, to a voltage value, a pressure value or the like.

According to the invention, "detachably receiving" is understood as a separable or dividable conjunction or association between the catheter and the implant. An example for a separable or dividable conjunction is crimping a stent onto a catheter for advancing or inserting the stent to the implantation site.

The catheter according to the invention advantageously allows for a controlled unfolding or decollapsing, respectively, and re-folding or re-collapsing, respectively, (which can also encompass or include expanding and returning back to a reduced diameter) of the implant, for example, when being arranged inside the implant. Thus, it is advantageously possible to return or bring the implant back to a smaller diameter again and thus re-implant it after its expansion or unfolding, i. e., to shift it at the implantation site. If there should be detected during implantation that an implant of wrong size or design or construction, respectively, had been chosen, the implant could advantageously be replaced even after its expansion/unfolding.

Thereby, the catheter can be connected to or communicate, respectively, with the implant via the means for controlling. The unfolding or decollapsing, respectively, and the folding or collapsing, respectively, of the implant can be performed without the aid of an outer sleeve.

The catheter can comprise a plastic or synthetic material or a copolymer or can be manufactured by means of two- or multiple-component technologies. According to the invention, the catheter can comprise a metal (steel or alloy). The catheter can be stiff; however, it can also be designed flexible or bendable, in order to be able to adapt it to or align it with defined or certain conditions. Thereby, the catheter can be manually bendable or it can be controlled for bending by means of a mechanism which can, e. g., be integrated in the catheter. The catheter can be bendable in a passive manner, e. g., by advancing or inserting it along the vessel or body lumen alone.

Independent of any other feature, i. e., without having to comprise any other feature in combination, the catheter can comprise a mechanically enforced or reinforced section, in particular in a tip area of the catheter, and in particular in a section which also comprises at least one of the passage means.

The catheter can have a circular or oval or rectangular cross-section. The catheter can also have a non-circular, a non-oval or a non-rectangular cross-section. Furthermore, the cross-section of the catheter can be unchanged across the whole catheter. However, it can also have two or three or more different cross-sections along its longitudinal axis and in particular in the area for receiving the implant.

The unfolding and folding of the implant which is controlled by the catheter can take place outside and inside a patient's body.

The catheter can be designed such as described in, e.g., US 2007/0100427 A1 by Perouse or in US 2005/0075731 A1 by Artof et al. By way of reference, the contents thereof are each subject-matter of the present invention. This particularly applies for the materials and (part) geometries given therein.

The catheter can be a one-lumen catheter; it can have no lumen and it can be a multi-lumen catheter. If it is a multi-lumen catheter, the catheter can be a two- or three- or multi-lumen catheter having equally or differently sized lumina in or regarding its cross-section.

Thus, in a preferred embodiment of the present invention, a catheter having a plurality of lumina in longitudinal direction or channels (hereinafter also designated in short: channel or channels) for guiding reins is proposed. The lumina or channels can serve for organizing and/or arranging or aligning, respectively, the reins. They can advantageously assure that the physician is always able to determine which one of the optionally same looking reins he holds in his hand or wants to operate. Hereto, he has only to orientate from which channel the respective rein comes out or leaves, respectively, or into which channel the rein enters.

In particular, the channels can serve for avoiding any disorientation or tangling, entangling, knotting or interloping, respectively, etc. of the reins with each other.

Furthermore, reins serving for the same or a common purpose during operation can be combined in the respective channels. Thus, reins which all have to be operated for effecting a certain behavior of the implant or the catheter can be guided through one channel. Reins which have to be operated for effecting another behavior of the implant or the catheter can be guided through another channel. Obviously, using the reins facilitates the operation of the implant or of the catheter by the physician.

Additionally, reins running to the implant can also be separated from reins running back from the implant.

Furthermore, providing the reins in a plurality of channels and their guidance therein can avoid a mutual interaction or interference, respectively, or the risk thereof. With the corresponding arrangement of the reins in separate channels it can, for example, be assured that, by pulling one rein running in a first channel, another rein is not unintendedly operated due to friction or any other interaction of the pulled rein with this other rein.

Furthermore, providing a plurality of channels for separately guiding reins can advantageously enable a separation of reins and other means such as, for example, a guiding wire. The function of the reins is thus not impacted or influenced, respectively, by further means and functions of the catheter, but—and this is not less advantageous—also vice-versa; i. e., it can also advantageously be avoided that the further means such as a guiding wire is impacted or influenced, respectively, by the presence or operation of the reins of the catheter.

Providing a plurality of channels for separately guiding reins can thus advantageously increase the precision during operation of the reins and thus the use of the catheter or of the implant.

In a further preferred embodiment of the present invention, a catheter comprising at least one passage means for letting pass one or more reins is proposed. As proposed in another preferred embodiment, the reins can serve for influencing the expansion and/or unfolding of the implant by changing a tension or stress, respectively, that is applied on the implant by the rein.

According to the invention, letting pass is also understood as passing or guiding through. A passage means can be a passage opening, an eye or loop, respectively, a deflecting or diverting section or the like.

According to the invention, a rein can comprise a polymer, a metal or a biological fiber material or can consist thereof. The rein or the reins can be absorbable.

According to the invention, a tension or a stress, respectively, which is applied to the implant by the rein, is also understood as a strain or in general any effect of the rein on the implant.

Whenever the present application refers to a rein, there can be meant more than one rein, for example, two, three, four, five or more reins.

The reins can also be provided functionally separated from the catheter.

The catheter can comprise an inner guiding means for the at least one rein.

In a preferred embodiment, the reins can leave or get out of the catheter at one side and/or at one end of the catheter through one or more passage means (especially, when those are designed as passage openings). Those passage means can be present in or on one or several planes perpendicular to the longitudinal axis of the catheter.

The catheter can comprise a device for cutting or tearing through the reins.

The implant can be a stent, in particular a valve supporting stent, in particular a cardiac valve supporting stent.

According to the invention, an implant, in particular a stent, is proposed, which comprises at least one means which is provided or prepared with the means of a catheter as defined above for controlling the expansion and/or unfolding of the implant from a first diameter to a second diameter and/or the return back from the second diameter to the first diameter in order to control the change of the diameter.

The advantages achievable herewith correspond at least to those of the catheter according to the invention. In order to avoid repetitions, it is therefore referred to the discussion thereof.

In a preferred embodiment, the implant comprises at least one guiding means which is prepared and suited for guiding at least one rein by which at least one section of the implant is expandable and/or decollapsible or unfoldable, respectively, from the first diameter to the second diameter and/or is returnable back from the second diameter to the first diameter by changing the tension or stress, respectively, or the strain applied to the rein.

The implant can be self-expanding, for example, it can be formed from or with a memory material, in particular nitinol, or materials which comprise nitinol. However, the implant can also be partly self-expanding, partly expandable by the use of an expanding means. The implant can exclusively be non-self-expanding. The implant can be foldable; the implant can be non-foldable.

The implant can comprise a biocompatible material, in particular a biocompatible stainless steel. The material can be bio-absorbable.

The implant can be designed with or without a means for encompassing or sandwiching parts of native valve sections (in particular heart valve leaflets). In particular, the implant can be designed with or without sections rising up or lowering down due to temperature and memory effect.

The one or several guiding means of the implant can be designed in form of guiding holes, guiding rings, eyes or loops, respectively, hooks or, generally spoken, guiding structures. They confer guidance to the rein which can be understood in the sense of directing the rein in one direction. According to the invention, guidance can also be understood such that the rein experiences stabilization along its extension. Thereby, the rein can be guided or directed, respectively, by the guiding means from an interior of the implant or stent, in particular from the catheter, to the implant structure (in particular to the exterior of the implant). The guiding means of the implant can be symmetrical (in particular circular, oval or square) or asymmetrical. The guiding means can be located on one plane, on several planes or on a spiral plane of the implant. Several guiding means can be designed equally or can be present in at least two different designs.

The implant or the stent can comprise a circular guiding means. The said can be designed in form of a channel which is, relative to the implant, open or closed to the outside, to the top or to the bottom. The guiding means can be closed or open and can have a symmetrical or asymmetrical form. The guiding means can be designed in form of a grid structure, a meander structure, a sinus wave structure, in particular one comprising 18 wave tips along a periphery, or the like. The guiding means can have a structure without a grid and/or without a meander and/or without a sinus wave structure. However, it can also comprise a sinus wave structure having a number of wave tips other than 18.

The implant can be a valve supporting stent and made from steel such as described in the patents U.S. Pat. Nos. 5,411,552, 5,840,081 and 6,168,614 B1 by Andersen et al. The stent can, however, also be a valve supporting self-expanding stent according to the disclosure of U.S. Pat. No. 7,018,406 B2 by Seguin et al. or of US 2005/0075731 A1 by Artof et al. The contents of the afore-mentioned documents are by way of reference herewith also subject-matter of the present invention or application, respectively. This particularly applies for material and (part) geometries of the implants and stents disclosed therein.

The reins can be guided or directed, respectively, along an interior of the catheter and can leave or get out of the catheter through the passage means. Then, the reins can be guided through the guiding units at or on the implant. The reins can be guided along a periphery or parts of a periphery in the guiding unit along the circumference of the implant. Then, the reins are guided back from outside through the passage means to the interior of the catheter. The reins can leave the catheter at its end proximal to the surgeon. The reins can leave the catheter at its end distal to the surgeon. The effect and in particular the strain of the reins and thus the controlled unfolding and the re-folding or reduction in the diameter of the stent can be controlled by means of a controlling means.

A rein can leave the catheter via a passage means arranged at the catheter and can be guided back into the catheter via the same passage means or via another passage means on the same or on another plane.

The reins can leave the catheter with their both ends.

The reins can leave the catheter with one end and can be connected to the catheter with the other end.

After cutting or tearing through or disengaging or notching, respectively, or by using any other kind of detaching or loosening the reins, the reins can be pulled back from the implant or stent and removed.

The reins can be cut or torn through by means of a device in the catheter, a device inside or outside the catheter (in particular a knife, a pair of scissors, by means of electrical voltage, by means of heat). A suited device can be arranged at or on the catheter.

With little or without any tension of the reins, the stent is unfolded or expanded. With tension being present, the stent is reduced in its diameter or is partly or completely re-folded.

According to the invention, a set is proposed which comprises at least one implant according to the invention, in particular a stent, and at least one catheter according to the invention as defined herein-above.

The advantages achievable therewith correspond to at least those of the catheter according to the invention. In order to avoid repetitions, it is therefore referred to the discussion thereof.

In a preferred embodiment of the set, the catheter is arranged in the center or substantially in the center of a cross-section or of any cross-section of the implant.

This center or central arrangement can relate to a state of use. It can relate to a non-unfolded or non-expanded state. It can, however, also relate to a completely expanded or unfolded state.

Furthermore, the state of use can be a state during positioning the implant—in particular during its rotation around a rotation center thereof—in order to precisely form the desired positional relation between the implant and the anatomic site at which the implant shall be implanted or come to rest in the body.

Arranging the catheter in the center of the implant can involve several advantages wherein a uniformly expanding of the implant is among those. Furthermore, with a centralized catheter, the implant can be controlled and positioned in a better way. The following example may point this out: In the case of a heart valve prosthesis as implant, it can be necessary to align or orientate, respectively, it relative to the commissures of the aortic root during the insertion of the prosthesis (the implant) supported by the catheter in such a way that the orientation thereof and the orientation of the valve leaflets arranged at the prosthesis are concerted or coordinated, respectively. For this purpose, the physician rotates the catheter around its longitudinal axis and, with a centrally arranged catheter, this rotation brings the heart valve prosthesis into a desired position relative to its orientation in its rotational direction, too. If the catheter is thereby not arranged in the center of the rotational-symmetrically constructed heart valve prosthesis, the heart valve prosthesis experiences a displacement in a radial or lateral direction. This displacement not only complicates achieving the desired orientation in the rotational direction, but also effects an undesired force and stress of circumjacent structures such as of the aortic root, of an already inserted receiving means for receiving and anchoring the prosthesis and the like. Centralizing the catheter in the center of the implant can advantageously counteract this. The relative relation between the catheter and the implant can remain unchanged. The occurrence of undesired displacements and forces can advantageously be avoided.

Centralizing the catheter in the center of the implant or the arrangement thereof in the center of the implant, respectively, can advantageously be used for checking the valve function with a catheter still being connected to the implant. The valve leaflets can unfold and close for a functional check without being hindered by the centrally arranged catheter; however, this would not be possible if the catheter would have been arranged at the edge, relative to a cross-section of the heart valve prosthesis. A position of the catheter other than the central position could result in a non-uniform opening and closing of the valve leaflets and complicate a functional check, falsify or distort, respectively, the result thereof or make it impossible. Such a functional check with a catheter still being connected to the heart valve is, however, of great importance and of great utility, because a revision or a re-positioning of the valve shall be possible when an unsatisfying position has been determined.

A central position of the catheter, relative to the cross-section of the implant, can also be advantageous in a folded or non-expanded state of the implant, because this position can allow a simplification of folding, crimping or the like of the implant. Thereby, the space requirement can advantageously be reduced, a damage of the implant or sections thereof (such as, in one embodiment, valve leaflets) can advantageously be avoided, etc.

Furthermore, a central position of the catheter, relative to the cross-section of the implant, can furthermore advantageously enable to control the position of the implant in such a way that the implant uniformly contacts the structure into which it shall be inserted at its periphery. Tension or force peaks which can damage the receiving tissue or complicate the insertion process of the implant can thus advantageously be avoided. The risk of damaging the implant (for example, valve leaflets) or injuring tissue can hereby advantageously be diminished.

BRIEF DESCRIPTION OF THE DRAWINGS

The invention will be illustrated exemplarily by use of the appended figures. Thereby, same or similar structures are denoted by the same reference numerals throughout the figures, wherein.

In a schematically simplified view.

DETAILED DESCRIPTION

Figure 1:
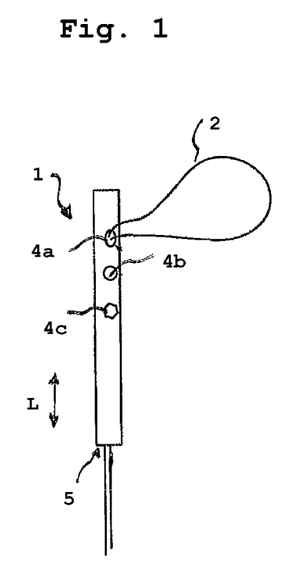
FIG. 1 shows a catheter according to the invention which comprises guiding units.

FIG. 1 shows a catheter 1 comprising a rein 2 which enters into the catheter 1 in the direction of a longitudinal axis L of the catheter 1 and leaves or gets out through passage means 4a, 4b and 4c, which can also serve for guiding the rein 2 which can, for example, be designed as a thread, on one or several planes or sections of the catheter 1. The passage means 4 can be symmetrical or asymmetrical. They can be designed round (4b), oval (4a), square (4e) or in any other suited form. The rein 2 which in the example of FIG. 1 enters through a longitudinal opening 5 into the catheter 1, can form a closed loop after leaving or emerging the passage means 4a, wherein the other end of the closed loop re-enters the catheter 1 at or through the same passage means 4a which hereby serves as an entry means and as an exit means at the same time, and leaves the catheter 1, for example, through the longitudinal opening 5 of the catheter 1.

Between the tip (at the top of FIG. 1) and the longitudinal opening 5 there is located a void 9 of the catheter 1 through which the rein or reins 2 can pass. The void 9 can extend at least from the longitudinal opening 5 to the (in FIG. 1) uppermost passage opening 4a.

Independent of any other feature, i. e., without having to comprise any other feature in combination, the catheter 1 can comprise a mechanically enforced or reinforced section, in particular in a tip area of the catheter and in particular in a section which also comprises at least one of the passage means.

Figure 2:
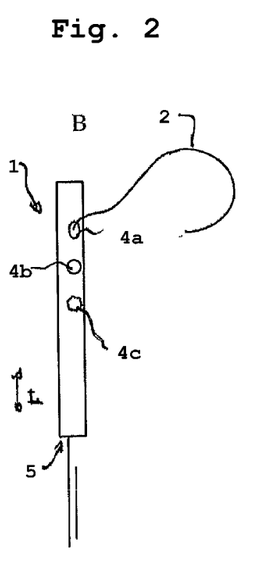
FIG. 2 shows the arrangement of FIG. 1.

FIG. 2 shows the arrangement of FIG. 1, wherein the rein 2 has been cut or torn through and can now be pulled back from a stent not shown here and out of the catheter 1.

Figure 3:
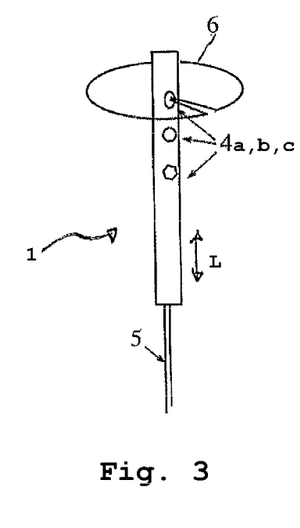
FIG. 3 shows the arrangement of FIG. 1.

FIG. 3 shows in turn the arrangement of FIG. 1 wherein the rein 2 is guided in form of a curve 6 around the stent (not shown) and returns through the same passage means 4a into the catheter 1. The rein 2 has no or only little tension at which the stent can be unfolded.

Figure 4:
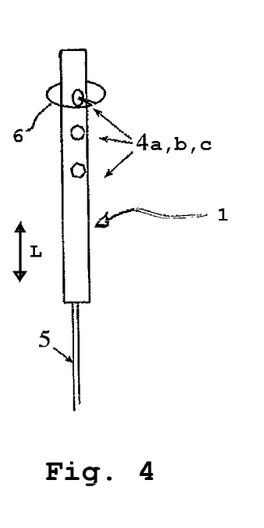
FIG. 4 shows the arrangement of FIG. 1.

FIG. 4 shows in turn the arrangement of FIG. 1 and in particular that of FIG. 3, wherein the rein 2 is tensioned or stressed in FIG. 4. The diameter of the stent (not shown) has been reduced again due to the effect of the curve 6. In case of a foldable stent, the stent is partly or completely re-folded.

Figure 5:
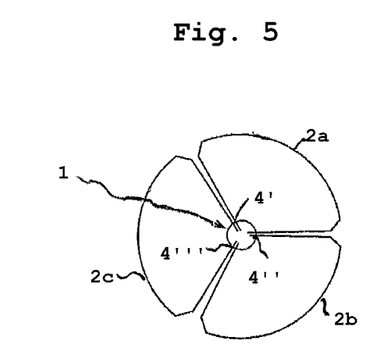
FIG. 5 shows an exemplarily run or extension, respectively, of three reins each about ⅓ of the periphery of the stent.

FIG. 5 shows an exemplary run or extension of three reins 2a, 2b and 2c each around ⅓ of the periphery of the stent. Each of these reins leaves the catheter through a passage means 4', 4" or 4'" and returns back through a different passage means.

Figure 6:
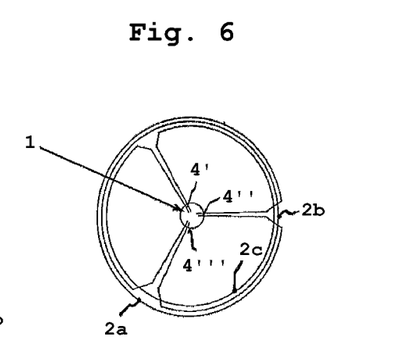
FIG. 6 shows the run or extension, respectively, of the reins along the complete periphery of the stent.

FIG. 6 shows the run or extension of the reins 2a, 2b and 2c around the complete periphery. Each of the reins emerges from the catheter 1 out of a passage means 4', 4" or 4'" and re-enters into the catheter 1 through the same passage means.

Figure 7:
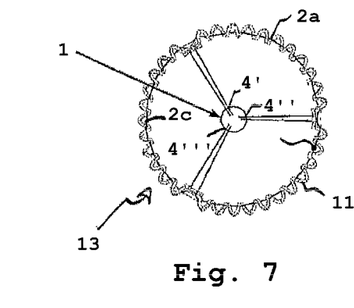
FIG. 7 shows the catheter of FIG. 5.

FIG. 7 shows the catheter 1 of FIG. 5. The reins 2a, 2b and 2c leave the catheter 1 and are guided at around ⅓ of the periphery in a guiding means 11 of the stent 13 (which is hereby exemplified by a half-open channel in form of a C).

Figure 8:
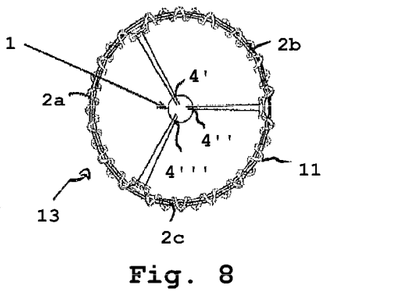
FIG. 8 shows the catheter of FIG. 6 comprising the stent of FIG. 7.

FIG. 8 shows the catheter 11 of FIG. 6 comprising the stent 13 of FIG. 7. The reins 2a, 2b and 2c leave the catheter 1 and are each guided back through the guiding means 11 along the complete circumference or the complete periphery of the stent 13 to the same passage means 11 at or on the catheter 1.

Figure 9:
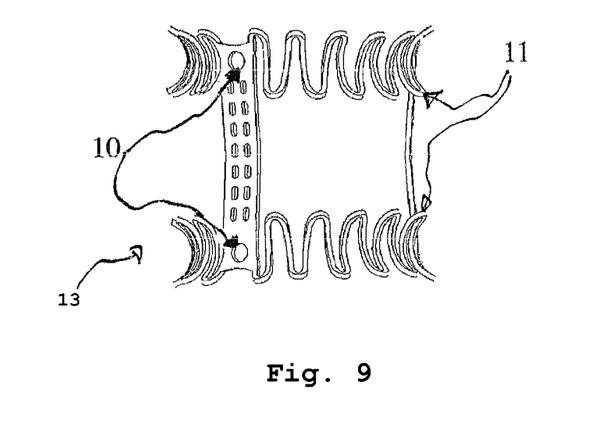
FIG. 9 shows an expandable stent which is reducible in its diameter again by the use of a means.

FIG. 9 shows an expandable stent 13 which is reducable in its diameter (in a plane perpendicular to a longitudinal axis of the stent which substantially corresponds to a laminar flow direction of the blood in an unbent or uncurved, respectively, vessel into which the stent has been inserted; the longitudinal direction also corresponds to the direction of the largest spatial extension of the stent before its unfolding outside the patient's body as well as after its unfolding in a comparable linear vessel section) again by the use of a means according to the invention which is not shown here. This stent 13 comprises two circular guiding means 11 each in form of a channel half-open to the outside—that can also be open to the stent—and two passage means 10 in form of round passages (thereby, the passage means 10 can also in any embodiment and independent of any other feature be designed non-round and can be present alone, in pairs, in a threesome or in a multi-some). Furthermore, the stent 13 can also comprise a number of guiding means 11 other than two, for example, one, three, four or more. The guiding means 11 can be arranged circularly, they can, however, also be provided in a non-circular manner. The guiding means 11 can be formed integrally with the stent, they can, however, also be fabricated separately. The passage means 10 can likewise be formed integrally with the stent or likewise be fabricated separately. The guiding means 11 can be designed in wave form, they can, however, also be fabricated in any other form, in particular in a non-wavy form.

The passage means 10 are arranged in sections of rods 12. They can be arranged at opposite ends of the rods 12, but also in every other section, for example, in a central area or section and not at the end of the rods. They can furthermore be arranged at a position of the stent 13 other than in or at the rods 12. Reins not shown here can be guided from an interior of the stent 13 through the passage means 10 to the outside and back again.

As an example of an implant, the stent 13 can comprise an arbitrary number of rods 12 which are all designed in the same way or have at least two different designs. The rods 12 can thereby be spaced apart from each other with the same distance. They can, however, also be arranged with at least two different distances from each other, respectively. The rods 12 can indeed comprise the passage openings 10, the latter can, however, also be provided separately from the rods 12. Likewise, the rods 12 can have openings, they can, however, also be designed without any passage openings. The stent 13 can be designed having rods which do not have any passage openings 10. The stent can further comprise at least one rod having passage openings and at least one rod not having any passage openings. The stent can comprise at least one rod which does not have any passage openings at all. The stent can comprise at least one rod which is arranged in or at the stent in a manner in which it is inclined to the longitudinal direction of the stent. The rods 12 can thereby extend in a manner in which they are bent or curved at both ends to the outside. Regardless of any other features, they can, however, extend such that they are not or at least not at both ends curved or bent to the outside. The rods 12 can be connected with or at their both ends to a wavy structure of the stent. Regardless of any other features, they can, however, not or at least not at both ends be connected to wavy structures.

Independent of any other feature, the stent 13 can be manufactured from flat material, for example, a material which has been cut with a laser, wherein, e.g., after having designed a pattern in the flat material, the material is reformed into a tube (optionally by connecting, such as welding, longitudinal sides of the former flat material lane or web, respectively). However, the stent 13 can also be fabricated from a tubular material directly.

Figure 10:
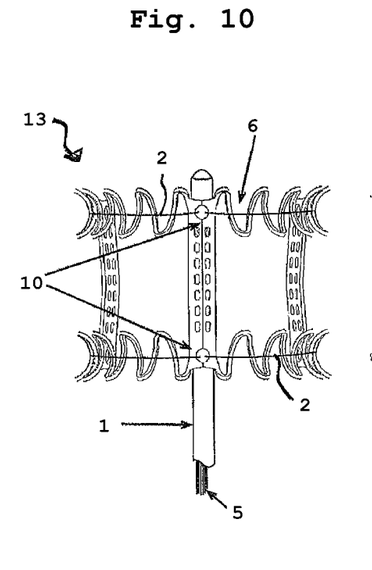
FIG. 10 shows the stent of FIG. 9.

FIG. 10 shows the stent 13 of FIG. 9. Two reins 2 have been guided around the stent 13 and return back to the catheter 1 through the same guiding means 10, respectively. The reins 2 exert no or only a small tension or stress on the stent 13 and the stent 13 is unfolded.

Figure 11:
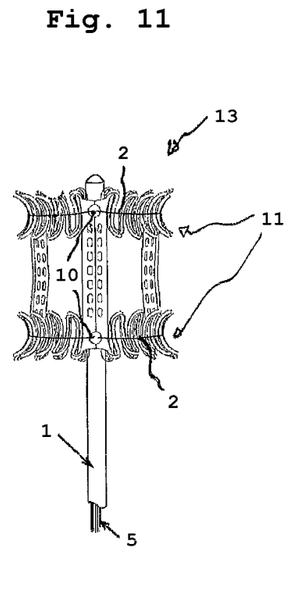
FIG. 11 shows tensioned reins and a reduced diameter of the stent.

In FIG. 11, the reins 2 are tensioned or stressed. The diameter of the stent 13 has been reduced. The stent 13 is re-folded at a larger extent. The reins 2 are guided in the guiding means 11 of the stent 13.

Figure 12:
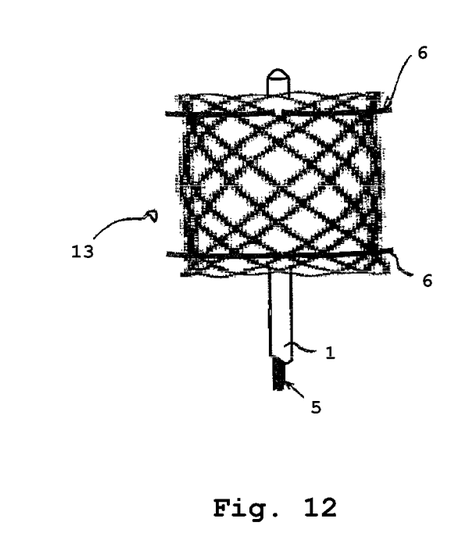
FIG. 12 shows a stent in the representation of FIG. 9.
Figure 13:
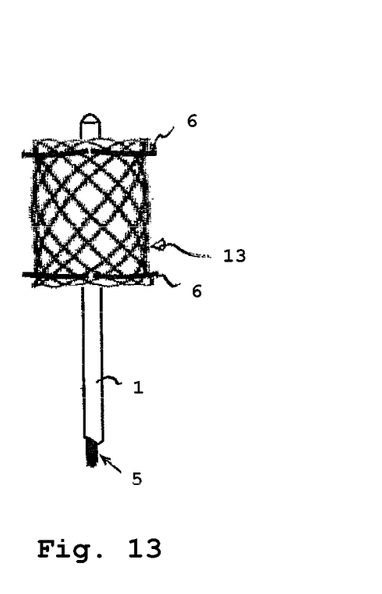
FIG. 13 shows a stent in the representation of FIG. 10.

FIG. 12 and FIG. 13 show a stent 13 in a representation corresponding to the representation of FIG. 9 and FIG. 10, respectively. Thereby, FIG. 9 shows the stent 13 in an expanded state, FIG. 10 shows the stent 13 with a reduced diameter again. The stent shown in FIG. 9 and FIG. 10 can thereby correspond to any stent known (with or without having valves). The stent 13 can in particular correspond to any unfoldable stent known.

In addition, in a schematically simplified manner, FIG. 12 shows a control unit for unfolding or expanding and in turn folding or reducing the stent 13 in its diameter in a controlled manner.

Figure 14:
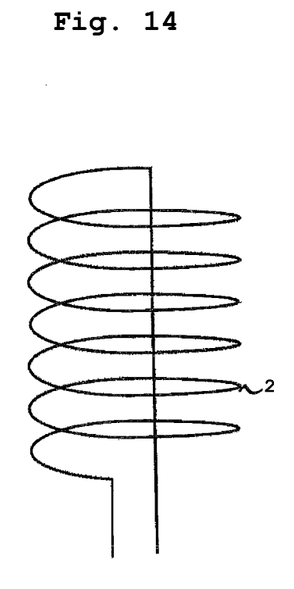
FIG. 14 shows another embodiment in which the reins are guided around the stent in a spiral form.

FIG. 14 shows that the reins 2 can also be guided in a spiral form around the stent 13. Here, only one rein 2 is shown which is guided in the interior of the stent 13 to the section in the front thereof. Then, the rein 2 is guided over the stent 13 at the outside and re-enters the catheter 1 (not shown here) again. The rein 2 is not or only a little tensioned or stressed and the stent (not shown here) is unfolded.

Figure 15:
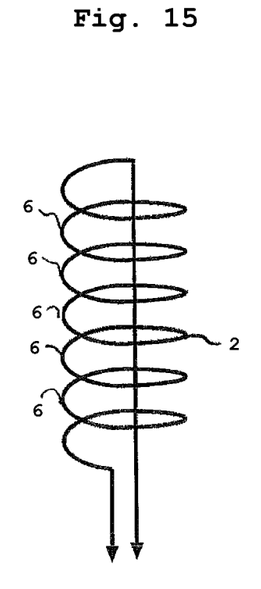
FIG. 15 shows the rein which is tensioned or stressed, respectively, on both ends, wherein the diameter of the spirally guided rein has been reduced.

In FIG. 15, the rein 2 is pulled up at both ends in the arrow direction and the diameter of the curve 6 of the spirally guided rein 2 has been reduced.

Figure 16:
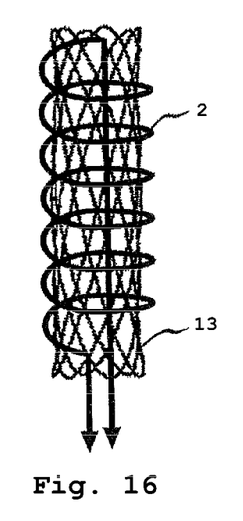
FIG. 16 shows the state of the rein of FIG. 15 about or around a stent.

FIG. 16 shows the state of the rein 2 of FIG. 15. The rein 2 (which is here also referred to as a thread) has been tensioned or stressed and the stent 13 has been folded or collapsed by use of the spirally guided rein 2.

Figure 17:
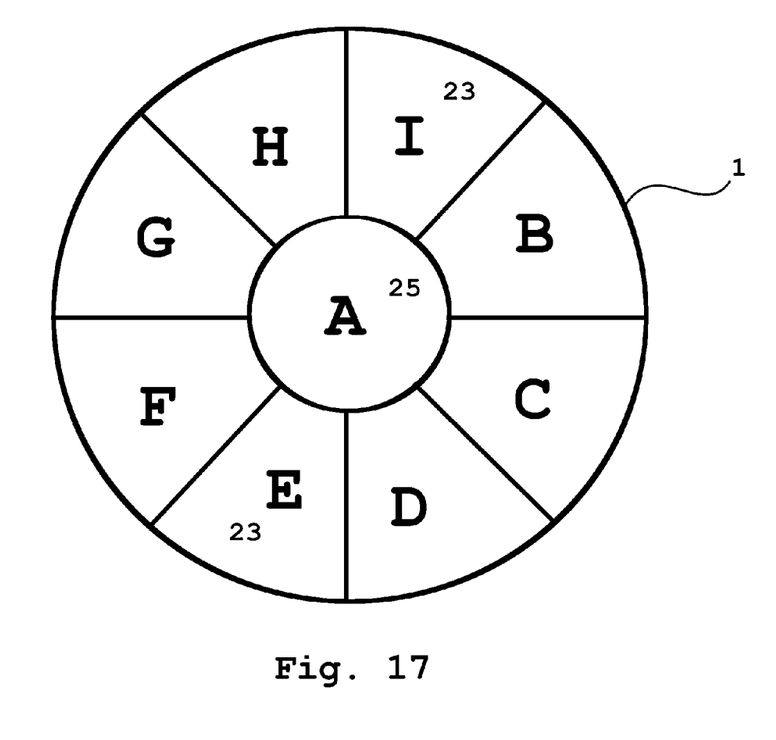
FIG. 17 shows a catheter according to the invention having a cross-section comprising a plurality of lumina.

FIG. 17 shows a catheter 1 according to the invention comprising a plurality of lumina or channels 23 for guiding through reins (not shown in FIG. 17) in a cross-section thereof. These channels 23 for the reins are designated by the letters B, C, D, E, F, G and H.

The lumina can be suited and prepared for guiding through reins for using the catheter.

The catheter 1 has a further lumen 25 in its center which is designated by the letter A and which is, in the embodiment shown, provided for receiving a means, such as a guiding wire, which is likewise not shown in FIG. 17.

The further lumen 25 which is shown in the center of the cross-section of catheter 1 in FIG. 17 is not limited to this arrangement. (One or more) lumen/lumina or channel(s) can also be arranged at the edge of the cross-section; two of them can be opposite to each other due to handling reasons, etc. Moreover, the catheter can comprise more than one lumen 25 for one or several further means, respectively.

The further means 25 can be a means other than a rein and/or not assuming a function in changing the diameter of the implant.

The further means 25 can be a means for cutting or tearing through the reins.

What is claimed is:

1. A catheter for detachably receiving an expandable implant, comprising:
    one or more reins;
    at least one longitudinally-extending lumen configured to guide at least one of the one or more reins;
    a side-wall defining an interior space;
    at least two openings formed through the side-wall of the catheter, the at least two openings providing a passage from the at least one lumen to an exterior of the catheter;
    an end opening provided at a longitudinal end of the catheter; and
    one or more control units, each of the one or more control units is configured to effect the one or more reins, respectively to control expanding of the expandable implant from a first diameter to a second diameter and/or recovering the expandable implant from the second diameter to the first diameter,
    wherein each of the one or more reins (i) enters the catheter through the end opening, (ii) extends through the at least one lumen along a length of the catheter, (iii) exits the at least one lumen through one opening of the at least two openings to the exterior of the catheter, (iv) continues to extend around at least a portion of a periphery of the catheter in a plane perpendicular to a longitudinal axis of the catheter with the catheter as an extending center thereof, (v) re-enters the at least one lumen into the interior space of the catheter, and (vi) leaves the catheter through the end opening,
    wherein an outer portion of each of the one or more reins that extends outside of the catheter has an outer periphery,
    wherein the outer peripheries of all of the outer portions are formed in the plane perpendicular to the longitudinal axis of the catheter; the outer peripheries of all of the outer portions form a generally complete circle, and
    wherein the catheter is disposed in a center of the generally complete circle.

2. The catheter according to claim 1, wherein the expanding of the expandable implant is controllable by changing tension or stress, respectively, of the one or more reins.

3. The catheter according to claim 1, comprising at least one inflatable means, in particular an inflatable balloon, for expanding the expandable implant.

4. The catheter according to claim 1, which is suited and/or prepared for a connection to a control device for controlling the expanding of the expandable implant from the first diameter to the second diameter and/or the recovering of the expandable implant from the second diameter to the first diameter, in particular for controlling tension or stress, respectively, applied to the one or more reins and/or the strain applied to the one or more reins.

5. The catheter according to claim 1, comprising the at least one lumen or a channel for receiving a guiding device, a cutting device, or a tearing device.

6. The catheter according to claim 1, comprising at least two additional openings formed through the side-wall of the catheter that provide an additional passage from the at least one lumen to the exterior of the catheter, wherein the at least two additional openings are located at different heights of the side-wall of the catheter.

7. The catheter according to claim 1, wherein the catheter further comprises a plurality of channels for guiding the one or more reins.

8. The catheter according to claim 1, wherein two reins of the one or more reins both enter or leave a same opening of the at least two openings.

9. The catheter according to claim 1, wherein the catheter includes three openings in a plane perpendicular to a longitudinal axis of the catheter.

10. The catheter according to claim 1, wherein each of the at least one rein extends around the catheter, enters and leaves a same opening of the at least two openings.

11. The catheter according to claim 1, wherein the catheter includes three openings, each of the three openings is located in a plane perpendicular to a longitudinal axis of the catheter, and each of the plane where each of the three openings is located is in parallel to each other.

12. A medical device assembly, comprising:
    at least one catheter according to claim 1; and
    at least one expandable implant, in particular a stent.

13. The medical device assembly according to claim 12, further comprising a memory shape material, in particular nitinol.

14. The medical device assembly according to claim 12, wherein the at least one expandable implant comprises a section which is prepared and suitable for being expandable and/or recoverable to a reduced diameter by use of the one or more reins in a controlled manner.

15. The medical device assembly according to claim 12, wherein the catheter is arranged in a center of a cross-section of the at least one expandable implant.

16. A system comprising;
    a catheter; and
    an implant, the catheter being configured for detachably receiving the implant, which is expandable, wherein the catheter comprises:
    one or more reins;
    at least one longitudinally-extending lumen configured to guide at least one of the one or more reins;
    a side-wall defining an interior space;
    at least two openings formed through the side-wall of the catheter, the at least two openings providing a passage between the at least one lumen and an exterior of the catheter;
    an end opening provided at a longitudinal end of the catheter; and
    one or more control units, each of the one or more control units is configured to effect the one or more reins, respectively to control expanding of the implant from a first diameter to a second diameter and/or recovering the implant from the second diameter to the first diameter,
    wherein each of the one or more reins (i) enters the catheter through the end opening, (ii) extends through the at least one lumen along a length of the catheter, (iii) exits the at least one lumen through one opening of the at least two openings to the exterior of the catheter, (iv) continues to extend around at least a portion of a periphery of the catheter in a plane perpendicular to a longitudinal axis of the catheter with the catheter as an extending center thereof, (v) re-enters the at least one lumen into the interior space of the catheter, and (vi) leaves the catheter through the end opening,
    wherein an outer portion of each of the one or more reins that extends outside of the catheter has an outer periphery,
    wherein the outer peripheries of all of the outer portions are formed in the plane perpendicular to the longitudinal axis of the catheter; the outer peripheries of all of the outer portions form a generally complete circle, and wherein the catheter is disposed in a center of the generally complete circle.

17. The system according to claim 16, comprising a memory shape material, in particular nitinol.

18. The system according to claim 16, wherein the implant comprises a section of the stent which is prepared and suitable for being expandable and/or recoverable to a reduced diameter by use of the one or more reins in a controlled manner.

19. The system according to claim 16, the catheter comprising at least two additional openings provided on the side-wall of the catheter that provide an additional passage from the at least one lumen to the exterior of the catheter, wherein the at least two additional openings are located at different heights of the side-wall of the catheter.

20. The system according to claim 16, wherein the catheter further comprises a plurality of channels for guiding the one or more reins.

21. A catheter for detachably receiving an implant, comprising:
   one or more reins;
   at least one longitudinally-extending lumen configured to guide at least one of the more or more reins;
   at least two openings formed through a side-wall of the catheter, the at least two openings providing a passage from the at least one lumen to an exterior of the catheter;
   an end opening provided at a longitudinal end of the catheter; and
   one or more control units, each of the one or more control units is configured to effect the one or more reins, respectively to control expanding of the implant from a first diameter to a second diameter and/or recovering the implant from the second diameter to the first diameter,
   wherein each of the one or more reins (i) enters the catheter through the end opening, (ii) extends through the at least one lumen along a length of the catheter, (iii) exits the at least one lumen through one opening of the at least two openings to the exterior of the catheter, (iv) continues to extend around at least a portion of a periphery of the catheter in a plane perpendicular to a longitudinal axis of the catheter with the catheter as an extending center thereof, (v) re-enters the at least one lumen into the interior space of the catheter, and (vi) leaves the catheter through the end opening, and
   wherein both ends of each of the at least one rein extend out of the longitudinal end of the catheter.

\* \* \* \* \*